United States Patent
Ge et al.

(10) Patent No.: US 11,525,142 B2
(45) Date of Patent: Dec. 13, 2022

(54) ***ZEA MAYS* NLP TRANSCRIPTION FACTOR ZMNLP5 AND USE THEREOF**

(71) Applicant: JIANGSU ACADEMY OF AGRICULTURAL SCIENCES, Nanjing (CN)

(72) Inventors: Min Ge, Nanjing (CN); Yuancong Wang, Nanjing (CN); Yuhe Liu, Washington, DC (US); Han Zhao, Nanjing (CN)

(73) Assignee: JIANGSU ACADEMY OF AGRICULTURAL SCIENCES, Nanjing (CN)

( * ) Notice: Subject to any disclaimer, the term of this patent is extended or adjusted under 35 U.S.C. 154(b) by 0 days.

(21) Appl. No.: 16/935,109

(22) Filed: Jul. 21, 2020

(65) Prior Publication Data

US 2020/0347398 A1    Nov. 5, 2020

Related U.S. Application Data

(63) Continuation-in-part of application No. PCT/CN2019/075784, filed on Feb. 22, 2019.

(51) Int. Cl.
*C12N 15/82*    (2006.01)

(52) U.S. Cl.
CPC ............................ *C12N 15/8271* (2013.01)

(58) Field of Classification Search
None
See application file for complete search history.

(56) References Cited

U.S. PATENT DOCUMENTS

2015/0143578 A1* 5/2015 Kraiser .............. C12N 15/8261
536/23.6

OTHER PUBLICATIONS

Ge et al. Genome-wide analysis of maize NLP transcription factor family revealed the roles in nitrogen response. Plant Growth Regul. (2018) 84:95-105. Published online: Sep. 20, 2017. (Year: 2018).*

Yu et al. Overexpression of *Arabidopsis* NLP7 improves plant growth under both nitrogen-limiting and -sufficient conditions by enhancing nitrogen and carbon assimilation. Sci. Rep. Jun. 13, 2016;6:27795. (Year: 2016).*
Cao et al. Overexpression of the Maize ZmNLP6 and ZmNLP8 Can Complement the *Arabidopsis* Nitrate Regulatory Mutant nlp7 by Restoring Nitrate Signaling and Assimilation. Front. Plant Sci. Oct. 5, 2017;8:1703. (Year: 2017).*
Transcript: GRMZM2G042278_T01, downloaded Apr. 1, 2021 from Protein Families Involved in the Transduction of Signalling (ProFITS) in the maize genome, http://bioinfo.cau.edu.cn/ProFITS/. (Year: 2021).*
Guana et al., "Interacting TCP and NLP transcription factors control plant response to nitrate availability," *Proc Natl Acad Sci USA* 114(9):2419-2424 (2017).
Hachiya et al. "*Arabidopsis* root type ferredoxin: NADP(H) oxidoreductase 2 is involved in detoxification of nitrite in roots," *Plant and Cell Physiology*, 57(11):2440-2450 (2016).
Liu et al., "Discovery of nitrate-CPK-NLP signaling in central nutrient-growth networks," *Nature* 545(7654):311-316 (2017).
Marchive et al. "Nuclear retention of the transcription factor NLP7 orchestrates the early response to nitrate in plants," *Nature Communications* 4:1713 (2013).
Yan et al., "NIN-like protein 8 is a master regulator o nitrate-promoted seed germination in *Arabidopsis*," *Nature Communications* 7:13179 (2016).

* cited by examiner

*Primary Examiner* — Cynthia E Collins
(74) *Attorney, Agent, or Firm* — McDermott Will & Emery LLP

(57) ABSTRACT

The present invention clones a gene ZmNLP5 from maize, which plays an important regulatory role in nitrogen assimilation, and the open reading frame of which has a DNA sequence shown as SEQ ID NO:1. The transcription factor protein encoded by the ZmNLP5 gene has an amino acid sequence shown as SEQ ID NO:2. The uses of the maize NLP transcription factor ZmNLP5 mentioned above in promoting expression of a nitrogen metabolic key enzyme gene ZmNIR1.1, in promoting expression of a nitrogen metabolic key enzyme gene ZmNIR1.2, in promoting expression of a nitrogen metabolic key enzyme gene ZmNR1.1, in promoting expression of a nitrogen metabolic key enzyme gene ZmNR1.2, in improving nitrogen assimilation in maize, and in promoting elongation growth of maize root in deficient nitrogen environment are further provided.

5 Claims, 5 Drawing Sheets

Specification includes a Sequence Listing.

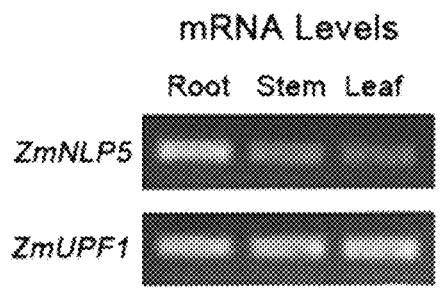
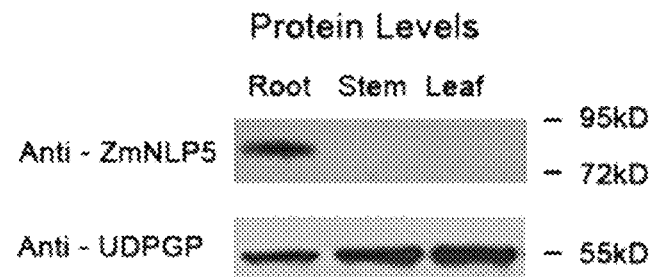
FIG. 1A
FIG. 1B
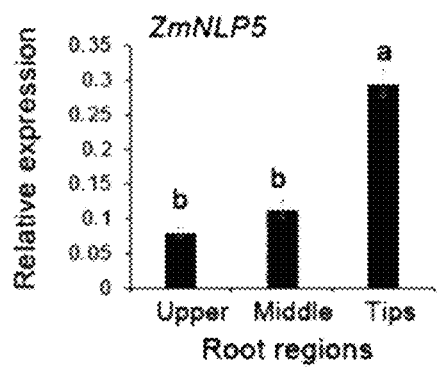
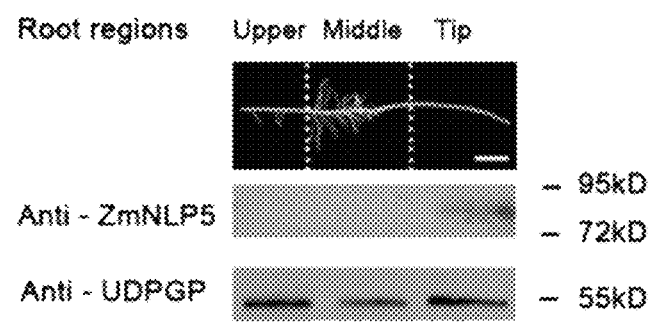
FIG. 1C
FIG. 1D
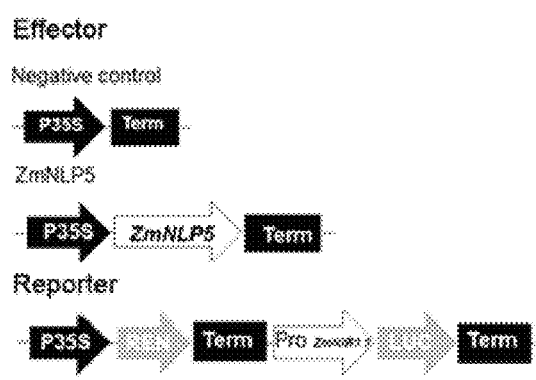
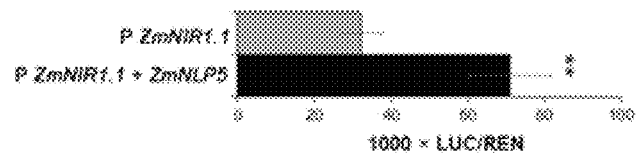
FIG. 2A
FIG. 2B

ZEA MAYS NLP TRANSCRIPTION FACTOR ZMNLP5 AND USE THEREOF This application is the continuation in part of International Application No. PCT/CN2019/075784 Filed on 22 Feb. 2019 which claims priority to Chinese Application No. CN 201811413552.X filed on 26 Nov. 2018, the entire contents of each of which are hereby incorporated by reference.

FIELD OF TECHNOLOGY

The present invention relates to the technical field of molecular genetics, specifically to the technical field of maize NLP transcription factors, in particular to a maize NLP transcription factor ZmNLP5 and applications thereof.

DESCRIPTION OF RELATED ARTS

Nitrogen (N) is a macronutrient element necessary for plant growth and development, and the maize production relies heavily on nitrogen fertilizers. However, the excessive application of the nitrogen fertilizers not only increases economic costs of farmers, but also causes different degrees of pollution to the environment. As such, improving efficiency of N use in maize crop production is critical for a sustainable agriculture.

NLPs are a kind of plant-specific transcription factors, which play important regulatory roles in plant nitrogen metabolic pathways. By ChIP-chip analysis Marchive et al. found that AtNLP7 binds to about 851 genes and preferentially binds to the transcription start sites of these target genes. Moreover, many target genes were involved in nitrogen signaling and metabolic pathways, such as LBD37/38, NRT1.1, NIA1, etc. (Marchive C, Roudier F, Castaings L, et al. 2013. Nuclear retention of the transcription factor NLP7 orchestrates the early response to nitrate in plants. *Nature Communications* 4, 1713). Yan et al. found that AtNLP8 was a key regulator of nitrate signaling during seed germination, directly binds to the promoter of an abscisic acid catabolic enzyme gene (CYP707A2) and activate the transcription of this gene (Yan D, Easwaran V, Chau V, et al. 2016. NIN-like protein 8 is a master regulator of nitrate-promoted seed germination in *Arabidopsis*. *Nature Communications* 7, 13179). Under deficient nitrogen (DN) conditions, an important transcription factor TCP20 has been found to interact with the AtNLP6/AtNLP7 heterodimer, and the TCP20-AtNLP6/AtNLP7 complex accumulates in nucleus, correlating with the regulation of the mitotic cyclin gene CYCB1; 1 and the nitrate signaling and assimilation genes (Guana P Z, Ripolla J J, Wang R H, et al. 2017. Interacting TCP and NLP transcription factors control plant responses to nitrate availability. *Proc Natl Acad Sci USA* 114(9): 2419-2424). In addition, the $NO^{3-}$-CPK-NLP regulatory network was found in *Arabidopsis*, wherein $NO^{3-}$ triggered specific $Ca^{2+}$-CPK signaling, which led to the phosphorylation of NLPs, and the $NO^{3-}$-CPK-NLP signaling pathway played important roles in regulating plant nutrient-growth networks (Liu K H, Niu Y, Konishi M, et al. 2017. Discovery of nitrate-CPK-NLP signaling in central nutrient-growth networks. *Nature,* 545 (7654): 311-316).

In conclusion, the NLP genes play crucial roles in regulating nitrogen metabolism. However, there are few research reports on functions of the NLP genes in maize, whose production is highly dependent on nitrogen fertilizers. Therefore, the functions of these genes need to be clarified in order to improve the nitrogen use efficiency in maize, and ultimately increase the maize yield.

SUMMARY OF THE INVENTION

In order to overcome the above mentioned shortcomings of the prior art, one object of the present invention is to provide a maize NLP transcription factor ZmNLP5, which can promote expressions of nitrogen metabolic key enzyme genes, improve nitrogen assimilation in maize, promote elongation growth of maize root in deficient nitrogen environment, and is suitable for large-scale popularization.

Another object of the present invention is to provide a use of the maize NLP transcription factor ZmNLP5 in promoting expression of a nitrogen metabolic key enzyme gene ZmNIR1.1 (*Zea mays* nitrite reductase 1.1), so as to promote the expression of the nitrogen metabolic key enzyme gene ZmNIR1.1, improve the nitrogen assimilation in maize, promote the elongation growth of the maize root in the deficient nitrogen environment, and is suitable for large-scale popularization.

Another object of the present invention is to provide a use of the maize NLP transcription factor ZmNLP5 in promoting expression of a nitrogen metabolic key enzyme gene ZmNIR1.2 (*Zea mays* nitrite reductase 1.2), so as to promote the expression of the nitrogen metabolic key enzyme gene ZmNIR1.2, improve the nitrogen assimilation in maize, promote the elongation growth of the maize root in the deficient nitrogen environment, and is suitable for large-scale popularization.

Another object of the present invention is to provide a use of the maize NLP transcription factor ZmNLP5 in promoting expression of a nitrogen metabolic key enzyme gene ZmNR1.1 (*Zea mays* nitrate reductase 1.1), so as to promote the expression of the nitrogen metabolic key enzyme gene ZmNR1.1, improve the nitrogen assimilation in maize, promote the elongation growth of the maize root in the deficient nitrogen environment, and is suitable for large-scale popularization.

Another object of the present invention is to provide a use of the maize NLP transcription factor ZmNLP5 in promoting expression of a nitrogen metabolic key enzyme gene ZmNR1.2 (*Zea mays* nitrate reductase 1.2), so as to promote the expression of the nitrogen metabolic key enzyme gene ZmNR1.2, improve the nitrogen assimilation in maize, promote the elongation growth of the maize root in the deficient nitrogen environment, and is suitable for large-scale popularization.

Another object of the present invention is to provide a use of the maize NLP transcription factor ZmNLP5 in improving nitrogen assimilation in maize, so as to improve the nitrogen utilization in maize, and is suitable for large-scale popularization.

Another object of the present invention is to provide a use of the maize NLP transcription factor ZmNLP5 in promoting elongation growth of maize root in deficient nitrogen environment, so as to promote the elongation growth of the maize root in the deficient nitrogen environment, and is suitable for large-scale popularization.

In order to realize the above aims, in a first aspect of the present invention, a maize NLP transcription factor ZmNLP5 is provided, wherein the amino acid sequence encoded by the coding sequence of the maize NLP transcription factor ZmNLP5 is shown as SEQ ID NO: 2.

There can be many nucleotide sequences encoding the amino acid sequence shown as SEQ ID NO: 2, preferably, the nucleotide sequence of the coding sequence of the maize NLP transcription factor ZmNLP5 is shown as SEQ ID NO: 1.

In a second aspect of the present invention, a use of the maize NLP transcription factor ZmNLP5 mentioned above in promoting expression of a nitrogen metabolic key enzyme gene ZmNIR1.1 is provided.

In a third aspect of the present invention, a use of the maize NLP transcription factor ZmNLP5 mentioned above in promoting expression of a nitrogen metabolic key enzyme gene ZmNIR1.2 is provided.

In a fourth aspect of the present invention, a use of the maize NLP transcription factor ZmNLP5 mentioned above in promoting expression of a nitrogen metabolic key enzyme gene ZmNR1.1 is provided.

In a fifth aspect of the present invention, a use of the maize NLP transcription factor ZmNLP5 mentioned above in promoting expression of a nitrogen metabolic key enzyme gene ZmNR1.2 is provided.

In a sixth aspect of the present invention, a use of the maize NLP transcription factor ZmNLP5 mentioned above in improving nitrogen assimilation in maize is provided.

In a seventh aspect of the present invention, a use of the maize NLP transcription factor ZmNLP5 mentioned above in promoting elongation growth of maize root in deficient nitrogen environment is provided.

The beneficial effects of the present invention are as follows:

a. The amino acid sequence encoded by the coding sequence of the maize NLP transcription factor ZmNLP5 of the present invention is shown as SEQ ID NO: 2, can promote expressions of nitrogen metabolic key enzyme genes, improve nitrogen assimilation in maize, promote elongation growth of maize root in deficient nitrogen environment, and is suitable for large-scale popularization.

b. The use of the maize NLP transcription factor ZmNLP5 of the present invention in promoting expression of a nitrogen metabolic key enzyme gene ZmNIR1.1 can promote the expression of the nitrogen metabolic key enzyme gene ZmNIR1.1, improve the nitrogen assimilation in maize, promote the elongation growth of the maize root in the deficient nitrogen environment, and is suitable for large-scale popularization.

c. The use of the maize NLP transcription factor ZmNLP5 of the present invention in promoting expression of a nitrogen metabolic key enzyme gene ZmNIR1.2 can promote the expression of the nitrogen metabolic key enzyme gene ZmNIR1.2, improve the nitrogen assimilation in maize, promote the elongation growth of the maize root in the deficient nitrogen environment, and is suitable for large-scale popularization.

d. The use of the maize NLP transcription factor ZmNLP5 of the present invention in promoting expression of a nitrogen metabolic key enzyme gene ZmNR1.1 can promote the expression of the nitrogen metabolic key enzyme gene ZmNR1.1, improve the nitrogen assimilation in maize, promote the elongation growth of the maize root in the deficient nitrogen environment, and is suitable for large-scale popularization.

e. The use of the maize NLP transcription factor ZmNLP5 of the present invention in promoting expression of a nitrogen metabolic key enzyme gene ZmNR1.2 can promote the expression of the nitrogen metabolic key enzyme gene ZmNR1.2, improve the nitrogen assimilation in maize, promote the elongation growth of the maize root in the deficient nitrogen environment, and is suitable for large-scale popularization.

f. The use of the maize NLP transcription factor ZmNLP5 of the present invention in improving nitrogen assimilation in maize can improve the nitrogen assimilation in maize, and is suitable for large-scale popularization.

g. The use of the maize NLP transcription factor ZmNLP5 of the present invention in promoting elongation growth of maize root in deficient nitrogen environment can promote the elongation growth of the maize root in the deficient nitrogen environment, and is suitable for large-scale popularization.

These and other objects, characteristics and advantages of the present invention will be elaborated sufficiently through the following detailed description, the drawings and the claims, and can be achieved with the means, the devices and their combinations particularly pointed out in the appended claims.

BRIEF DESCRIPTION OF THE DRAWINGS

FIG. 1A shows the analysis results of the expression patterns of the maize NLP transcription factor ZmNLP5 in different tissues: the expression levels of the mRNA of the ZmNLP5 gene in the different tissues detected by RT-PCR, with ZmUPF1 used as the internal reference gene;

FIG. 1B shows the analysis results of the expression patterns of the maize NLP transcription factor ZmNLP5 in different tissues: the expression levels of the ZmNLP5 protein in the different tissues detected by WB, with UDPGP used as the internal reference protein;

FIG. 1C shows the analysis results of the expression patterns of the maize NLP transcription factor ZmNLP5 in different tissues: the expression levels of the mRNA of the ZmNLP5 gene in different parts of the root detected by qPCR, with ZmUPF1 used as the internal reference gene;

FIG. 1D shows the analysis results of the expression patterns of the maize NLP transcription factor ZmNLP5 in different tissues: the expression levels of the protein of the ZmNLP5 protein in different regions of the root detected by WB, with UDPGP used as the internal reference protein;

FIG. 2A shows the maize NLP transcription factor ZmNLP5 regulating the gene encoding nitrite reductase 1.1 (ZmNIR1.1) and constructs used in the transcription activation assay: the schematic diagram of the effector and the reporter;

FIG. 2B shows the maize NLP transcription factor ZmNLP5 regulating the gene encoding nitrite reductase 1.1 (ZmNIR1.1) and constructs used in the transcription activation assay: the transient expression activity analysis result of the ZmNIR1.1 regulated by ZmNLP5;

DETAILED DESCRIPTION OF THE PREFERRED EMBODIMENT

Figure 3:
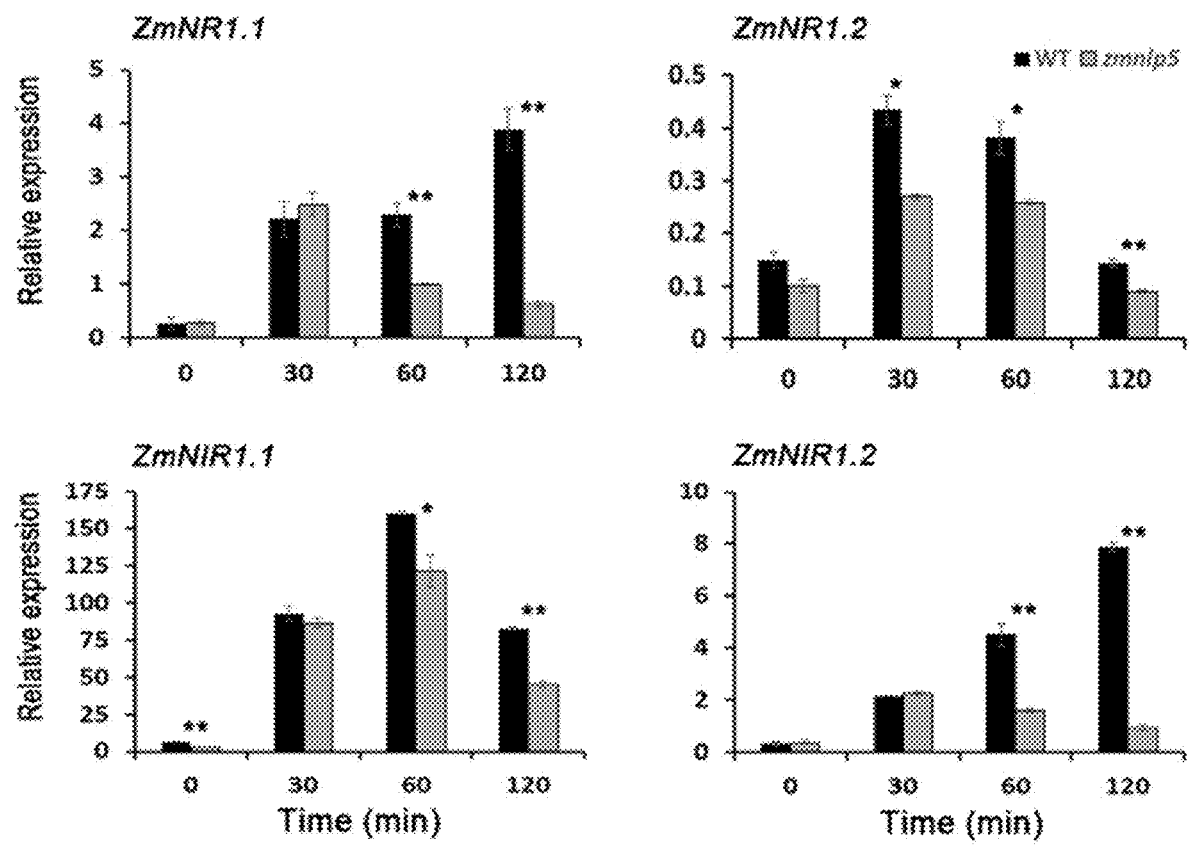
FIG. 3 shows the result of the effect of the maize NLP transcription factor ZmNLP5 on the expression levels of the nitrogen metabolic key enzyme genes in maize at seedling stage, wherein NR is the nitrate reductase, NIR is the nitrite reductase, one-week-old plant seedlings were grown in hydroponic culture treated with N starvation for two weeks, then treated by nitrate (15 mm $KNO_3$), and total RNA is extracted from samples collected from the roots at 0, 30, 60 and 120 min respectively. Levels of mRNA for ZmNR1.1, ZmNR1.2, ZmNIR1.1 and ZmNIR1.2 in the samples are detected by qPCR, ZmUPF1 is used as the internal reference gene, *P-Values≤0.05, ** P-Values≤0.01 by student's t-test [n=3]

In order to understand the technical content of the present invention clearly, the present invention is further exemplified by reference to the following examples.

The terms used in the present invention, unless otherwise specified, generally have the meanings commonly understood by those skilled in the art. In the embodiments, various processes and methods not described in detail are conventional methods well known in the art. Hereinafter, taking the maize material zmnlp5 in which the ZmNLP5 gene is mutated as an example, the preferred embodiments of the present invention are described, but are not limited to the present invention.

Embodiment 1 Cloning and Identifying the Maize ZmNLP5 Gene

Based on the previous research done by the present inventors (Ge M, Liu Y H, Jiang L, et al. 2018. Genome-wide analysis of maize NLP transcription factor family revealed the roles in nitrogen response. Plant Growth Regul, 84: 95-105), the ZmNLP5, which showed the most significant response to the N supply at the transcriptional level among the NLP family members, was selected as the research object. The maize elite inbred line B73 (obtained from Crop Molecular Breeding Laboratory, Institute of Agricultural Biotechnology, Jiangsu Academy of Agricultural Sciences) was used as the experimental material. To further isolate and clone the full-length cDNA sequence of the ZmNLP5 gene, primers were designed according to the sequence information of the ZmNLP5 gene (GRMZM2G042278) on the Phytozome website, and the specific scheme is as follows:

Samples were taken from the maize B73 plants at the seedling stage (V3 stage). After they were ground in liquid nitrogen, total RNA was extracted using the RNA isolation system kit (Promega), and then was reverse transcribed to cDNA using the reverse transcription kit prime Script™ RT Reagent kit (Takara). Using the obtained cDNA as the template, the PCR reaction was carried out using a primer pair for amplifying the open reading frame of ZmNLP5 as shown in SEQ ID NO:3 and SEQ ID NO:4, respectively. The PCR amplification mixtures contain the components as follows: 4.0 μl cDNA template (0.05 μg), 5.0 μl 10×PCR buffer, 2 μl each of the forward primer and the reverse primer (10 μmol/L), 4.0 μl 2.5 mmol/L dNTPs, 4.0 μl 25 mmol/L MgCl$_2$, 0.2 μL 5 u/μL rTaq, 28.8 μl ddH$_2$O (the total volume of one reaction is 50.0 μl). The PCR amplification conditions were as follows: 94° C. 3 min; 94° C. 40 s, 58° C. 40 s, 72° C. 3 min, 38 cycles; 72° C. 5 min. The sequences of PCR products were analyzed after they had been purified and sequenced. The results showed that the open reading frame of ZmNLP5 matches the nucleotide sequence (2268 bp in total) shown in the SEQ ID NO:1 and encodes 755 amino acids shown in SEQ ID NO:2.

Embodiment 2 Expression Patterns of ZmNLP5 in Different Tissues of Maize

RT-PCR, Quantitative real-time PCR (qPCR) and protein immunoblot assay (Western blot, WB) were used to detect the mRNA and the protein levels of ZmNLP5 in various tissues and different parts of one certain tissue of Maize. The maize inbred line W22, which was used as the experimental material, (obtained from Maize Genetics Cooperation Stock Center UniformMu Transposon Resource), was grown in hydroponic culture in the greenhouse of Jiangsu Academy of Agricultural Sciences. The modified Hoagland nutrient solution was employed as basic nutrient solution (5 mM $CaCl_2$), 2 mM $MgSO_4$, 0.05 mM EDTA-Fe—Na Salt, 0.5 mM $KH_2PO_4$, 50 µM $H_3BO_4$, 10 µM $MnCl_2$, 1 µM $ZnSO_4$, 0.3 µM $CuSO_4$, and 0.5 µM $Na_2MoO_4$), with 15 mM $KNO_3$ as sufficient nitrogen (SN) solution and 0.15 mM $KNO_3$ as deficient nitrogen (DN) solution, the differences in potassium supply were balanced with KCl. The nutrient solutions were changed every two days, and the routine management was adopted. Samples were taken from different tissues (root tissue, stem tissue, leaf tissue, and the root tip, the middle and the upper region of the root tissue) of the maize plants at the V3 stage growing in the SN solution, and were quick-frozen and ground in liquid nitrogen, then the total RNA and the total protein were extracted.

The process of the total RNA extraction was the same as that in the Embodiment 1. The housekeeping gene ZmUPF1 (GRMZM2G163444) was used as the internal reference gene for RT-PCR and qPCR analyses, its amplification primer pair includes a ZmUPF1 forward primer and a ZmUPF1 reverse primer, as shown in SEQ ID NO:5 and SEQ ID NO:6, respectively. RT-PCR analyses were carried out with the cDNA templates derived from different tissues of maize, and qPCR analyses were carried out with cDNAs from different parts of maize root as templates. The amplification primer pair of ZmNLP5-qPCR includes a ZmNLP5-qPCR forward primer and a ZmNLP5-qPCR reverse primer, as shown in SEQ ID NO:7 and SEQ ID NO:8, respectively. The primer pair used in the RT-PCR was the same primer pair of ZmNLP5-qPCR.

The total protein was extracted by Plant Nuclei Isolation/Extraction kit (Sigma), and the concentration of the total protein was quantified by BCA Protein Assay Kit (Beyotime). The total proteins extracted from the different tissues of the maize and the different regions of the maize root were separated by SDS-PAGE and transferred to a PVDF membrane (0.2 µm, Millipore, USA). Then the PVDF membrane, which the separated proteins were attached, was blocked and incubated with the primary antibody and then the secondary antibody. Finally, the chemiluminescence was detected by BeyoECL Plus (Beyotime). The dilution ratio of the ZmNLP5 specific antibody (the antibody is prepared by ABclonal technology of Shanghai Yingji Biotechnology Co., Ltd., and the rabbit source is the experimental Japanese white rabbit) is 1:1000, the dilution ratio of the marker antibody UDPGP (Agrisera) is 1:2000, and the dilution ratio of the secondary antibody is 1:3000.

The results showed that the ZmNLP5 transcripts were detected in all three tissues (root, stem and leaf), with significantly more abundance in the roots than in the stems or leaves (FIG. 1A). The ZmNLP5 protein was mainly detected in the root, no visible ZmNLP5 protein signal can be detected in the stem and the leaf (FIG. 1B). In addition, the accumulation of the ZmNLP5 mRNA in the root tip region was significantly higher than those in the middle and upper regions of the root (FIG. 1C), the similar distribution pattern of ZmNLP5 protein was found in the root tissue as well (FIG. 1D).

Embodiment 3 Transient Expression Activity Analysis of ZmNLP5 in the Regulation of the Gene Encoding Nitrite Reductase 1.1 (ZmNIR1.1)

3.1 Vector Construction:

Effector vector: the ZmNLP5 cDNA isolated and cloned in Embodiment 1 was constructed in the pMDC83-35S vector to generate a 35S promoter-driven ZmNLP5 effector, using the homologous recombination method. The pMDC83-35S empty vector was used as the negative control (FIG. 2A). The primer pair for constructing the effector vector included a ZmNLP5-pMDC83 forward primer and a ZmNLP5-pMDC83 reverse primer, as shown in SEQ ID NO:9 and SEQ ID NO:10, respectively.

Reporter vector: a DNA fragment of about 1200 bp upstream of the start codon of the nitrite reductase gene ZmNIR1.1 (GRMZM2G079381) was isolated and cloned, using the method in Embodiment 1. The cloning primer pair includes ZmNIR1.1-HindIII-F and ZmNIR1.1-BamHI-R. Their sequences are shown as SEQ ID NO:11 and SEQ ID NO:12, respectively. The nucleotide sequence shown as SEQ ID NO:13 was identified by PCR and sequencing. The DNA fragment containing the promoter region of ZmNIR1.1 was constructed into the pGreenII0800-LUC vector by the homologous recombination method. The vector constructing primer sequences are shown as SEQ ID NO:14 and SEQ ID NO:15. The constructed vector was used as the report vector (ZmNIR1.1::LUC), which contains the renilla luciferase gene (REN: the internal reference gene) driven by the 35S promoter and the firefly luciferase gene (LUC: the reporter gene) driven by the promoter of ZmNIR1.1 (FIG. 2A).

3.2 Observation of the Activities of the Dual Luciferases in Onion Epidermal Cells Transformed by Biolistic Bombardment The gold powders coated with the DNA plasmids (35S::ZmNLP5 and ZmNIR1.1::LUC, the control plasmids are 35S and ZmNIR1.1::LUC) were used to bombard the epidermal cells of the onion (*Allium cepa*), the model of the gene gun was PDS-1000 system (Bio-Rad, Hercules, Calif.). After the bombardment, the samples were incubated in dark at 25° C. for 8 h, and the activities of LUC and REN were detected respectively according to the instruction of the dual luciferase reporter gene detection kit (Biyuntian). Finally, the luminescent intensities were measured by the microplate reader (Tecan M200).

The results of the dual-luciferase transient transcriptional activity assay showed that compared with the control experiment, the co-expression of 35S::ZmNLP5 and ZmNIR1.1::LUC significantly increase the activity of LUC (P-Values≤0.01, t-test) (FIG. 2B), indicating that ZmNLP5 can activate the transcription of the ZmNIR1.1 gene.

Embodiment 4 Use of the Maize NLP Transcription Factor ZmNLP5 in Improving Nitrogen Assimilation in Maize Taking the maize material zmnlp5 (No.: UFMu-01175, http://www.maizegdb.org/uniformmu, W22 background, the mutant and wild-type seeds both were obtained from Maize Genetics Cooperation Stock Center UniformMu Transposon Resource) in which the ZmNLP5 gene is mutated as an example, the preferred embodiments of the present invention are described, but not limited to the present invention.

Nitrate is the primary nitrogen source for plants (such as maize), and reduced to ammonium by the nitrate reductase (NR) and the nitrite reductase (NIR) after entering into the plant root cells. The ammonium is assimilated finally into amino acids through a series of continuous reactions. Therefore, NR and NIR are the key enzymes for the nitrogen assimilation in maize. In Embodiment 3, it has been proved that ZmNLP5 has the role of activating the transcription of the nitrite reductase gene (ZmNIR1.1). In order to further clarify the effect of ZmNLP5 on the nitrogen response and assimilation pathways, we detected the transcript levels of the ZmNR gene and the ZmNIR gene in the wild-type (WT) plant and the mutant (zmnlp5) plant at the seedling stage after nitrate stimulation, and the qPCR primer pair of the ZmNR1.1 gene is shown as SEQ ID NO:16 and SEQ ID NO:17, the qPCR primer pair of the ZmNR1.2 gene is shown as SEQ ID NO:18 and SEQ ID NO:19, the qPCR primer pair of the ZmNIR1.1 gene is shown as SEQ ID NO:20 and SEQ ID NO:21, and the qPCR primer pair of the ZmNIR1.2 gene is shown as SEQ ID NO:22 and SEQ ID NO:23. One-week-old WT and zmnlp5 plant seedlings were cultivated with DN solution for additional two weeks and then treated with nitrate (15 mM $KNO_3$). The transcriptional abundance of selected genes were monitored using qPCR at 0, 30, 60 and 120 min after N treatment. For each time point, three biological replicates were performed. As shown in FIG. 3, we detected the transcriptions of the four genes: ZmNR1.1 (GRMZM5G878558), ZmNR1.2 (GRMZM2G428027), ZmNIR1.1 and ZmNIR1.2 (GRMZM2G102959). The results show that the expression levels of the four genes at 60 min after the N treatment in the zmnlp5 mutant are significantly lower than those in the WT plant (P-Values≤0.05), and compared with the WT plant, at 120 min after the N stimulation, the transcript levels of the ZmNR1.1, ZmNR1.2, ZmNIR1.1 and ZmNIR1.2 genes in the zmnlp5 mutant plant were decreased by 83.85%, 36.73%, 45.83% and 88.37% respectively (FIG. 3). The up-regulations of the nitrogen assimilation key genes responding to the N stimulation are mitigated in the zmnlp5 mutant plants, indicating that the loss of the function of ZmNLP5 affects the nitrogen response and assimilation pathways of plants.

Figure 4A:
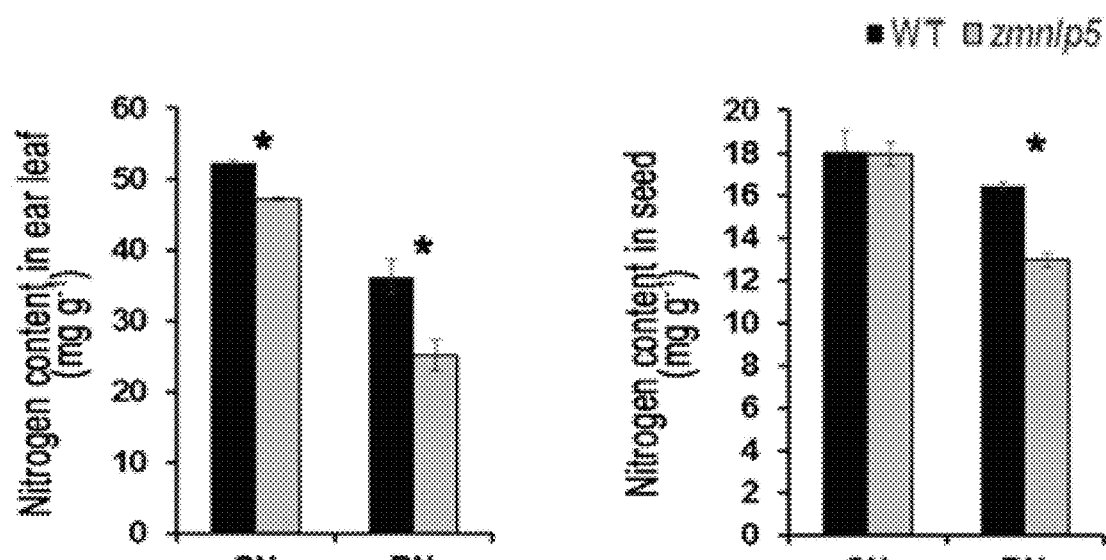
FIG. 4A shows the result of the effect of the maize NLP transcription factor ZmNLP5 on nitrogen contents of ear leaves and seeds in maize at maturity stage: the comparison diagram of the total nitrogen contents of the ear leaves and the seeds of the zmnlp5 mutant and the wild type (WT) plant under sufficient nitrogen (SN) and deficient nitrogen (DN) conditions, *P-Values≤0.05, ** P-Values≤0.01 by student's t-test [n=3]
Figure 4B:
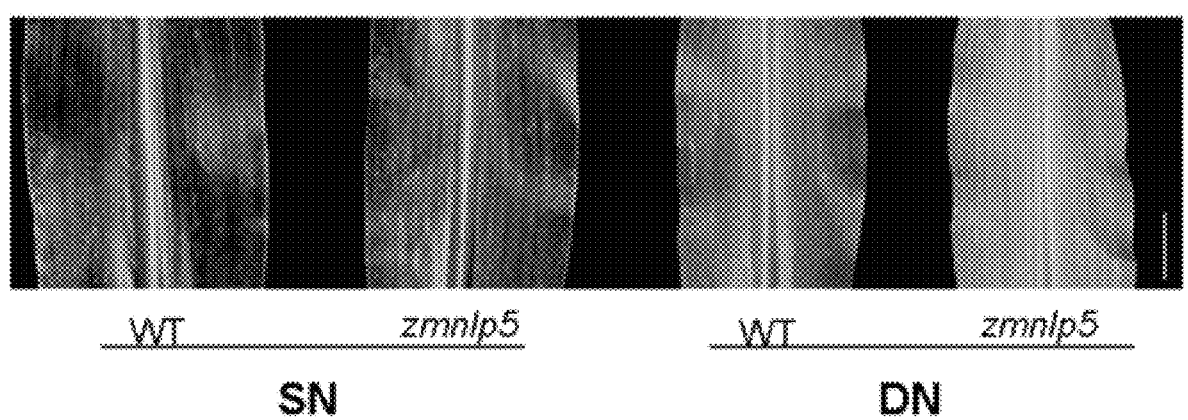
FIG. 4B shows the result of the effect of the maize NLP transcription factor ZmNLP5 on nitrogen contents of ear leaves and seeds in maize at maturity stage: Phenotypes of ear leaves in mature plants of WT and zmnlp5 under SN and DN conditions.
Figure 5A:
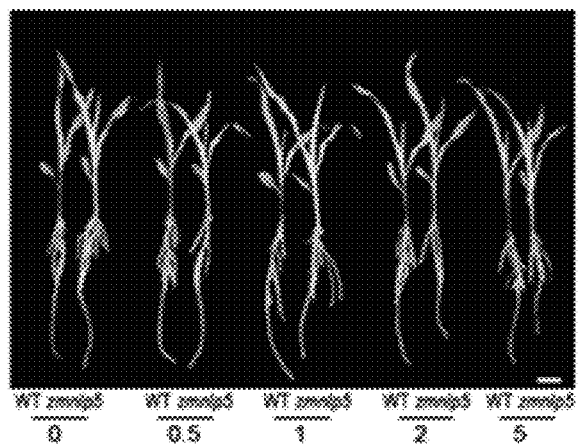
FIG. 5A shows the result of the effect of the maize NLP transcription factor ZmNLP5 on root length of maize at seedling stage: the comparison diagram of the phenotypes of the zmnlp5 mutant and the wild type plant treated with different nitrite concentrations, bar=2 cm.
Figure 5D:
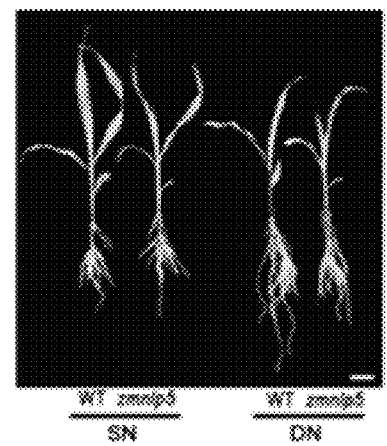
FIG. 5D shows the result of the effect of the maize NLP transcription factor ZmNLP5 on root length of maize at seedling stage: the comparison diagram of the phenotypes of the zmnlp5 mutant and the wild type material treated with SN and DN solutions, bar=2 cm.
Figure 5B:
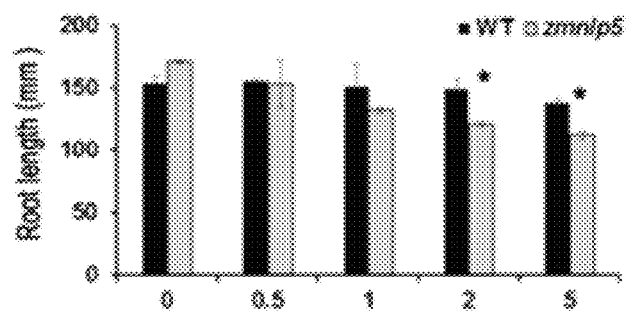
FIG. 5B shows the result of the effect of the maize NLP transcription factor ZmNLP5 on root length of maize at seedling stage: the comparison diagram of the root lengths of the zmnlp5 mutant and the wild type plant treated with different nitrite concentrations, *P-Values≤0.05 by student's t-test [n=3]
Figure 5E:
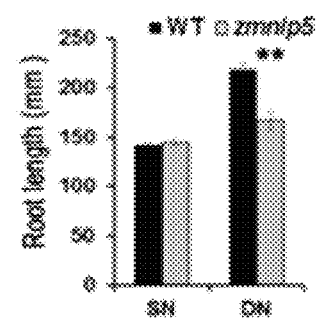
FIG. 5E shows the result of the effect of the maize NLP transcription factor ZmNLP5 on root length of maize at seedling stage: the comparison diagram of the root lengths of the zmnlp5 mutant and the wild type plant treated with SN and DN solution, ** P-Values≤0.01 by student's t-test [n=3]
Figure 5C:
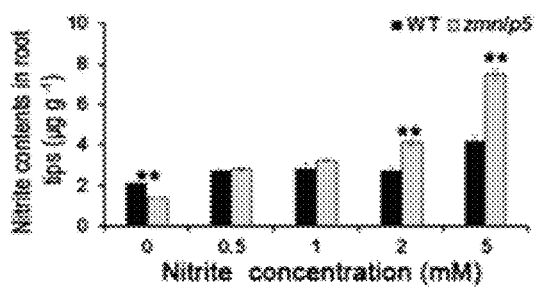
FIG. 5C shows the result of the effect of the maize NLP transcription factor ZmNLP5 on root length of maize at seedling stage: the comparison diagram of the root tip nitrite contents of the zmnlp5 mutant and the wild type plant treated with different nitrite concentrations, ** P-Values≤0.01 by student's t-test [n=3]
Figure 5F:
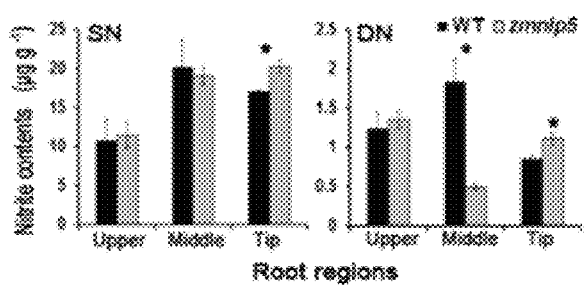
FIG. 5F shows the result of the effect of the maize NLP transcription factor ZmNLP5 on root length of maize at seedling stage: the comparison diagram of the nitrite contents in different parts of the roots of the zmnlp5 mutant and the wild type plant treated with SN and DN solution, *P-Values≤0.05 by student's t-test [n=3]

In addition, the wild-type (WT) and zmnlp5 mutant plants were planted under SN (SN: 15 mM $KNO_3$) and DN (DN: 0.15 mM $KNO_3$) conditions, respectively. The total nitrogen contents of the ear leaves and the seeds were measured by the Kjeldahl nitrogen determination method to explore the effect of ZmNLP5 on the nitrogen assimilation of mature plants. The results showed that the total nitrogen contents of the ear leaves of the zmnlp5 mutant plant were significantly lower than those of the WT plant (P-Values≤0.05) in both of the SN and DN conditions, and decreased by 14.53% and 21.31% respectively (FIG. 4). Under SN conditions, WT plants have similar N contents in seed kernels compared with that of zmnlp5 plants, whereas under DN conditions, zmnlp5 exhibited significantly lower N contents in seed kernels compared to that in the seeds of WT (P-Values≤0.05), and decreased by 21.09%. The ability of the nitrogen assimilation in the zmnlp5 mutants is significantly weakened (FIG. 4).

Embodiment 5 Use of the Maize NLP Transcription Factor ZmNLP5 in Promoting Elongation Growth of Maize Root in Deficient Nitrogen Environment In Embodiment 3, we showed that ZmNLP5 directly activates the expression of ZmNIR1.1 (FIG. 2), and in Embodiment 2, we found that ZmNLP5 is mainly expressed in the tip region of the root (FIG. 1). For in the nitrogen assimilation process, ZmNIR1.1 is the key enzyme to reduce nitrite to ammonium, and nitrite has certain cytotoxicity to the rapidly growing cells in the root tips (Hachiya T, Ueda N, Kitagawa M, et al. 2016. *Arabidopsis* root type ferredoxin: NADP (H) oxidoreductase 2 is involved in detoxification of nitrite in roots. Plant and Cell Physiology, 57(11): 2440-2450), it is suggested that ZmNLP5 may contribute, at least to some extent, to the elongation growth of plant root.

In order to test this hypothesis, we first studied the relationships between the root lengths and nitrite contents in the root tips of the WT and zmnlp5 mutant plants in different nitrite concentrations (0, 0.5, 1, 2 and 5 mM $KNO_2$). The root lengths and the root tip nitrite contents of the two-weed-old maize seedlings cultured in hydroponic nutrient solutions with different concentrations of nitrite were measured. The results showed that when the concentration of nitrite was higher than 2 mM, zmnlp5 accumulated more nitrite in the root tips than WT (P-Values≤0.01), the root length is also significantly reduced (P-Values≤0.05) (FIG. 5). These results suggested that in the zmnlp5 mutant, the activation of the nitrite reductase is mitigated due to the malfunction of ZmNLP5. Therefore, the nitrite could not be assimilated into ammonium in time, leading to a higher amount of nitrite in the root tip of the zmnlp5 mutant. When nitrite accumulates to a certain concentration, it would be toxic to the root tip cells, and eventually lead to the inhibition of the elongation growth of the root.

To further examine the roles of ZmNLP5 in modulating root growth in the plants under different nitrate supply, we measured the root lengths and the nitrite contents in the three-week-old WT seedlings and the mutant seedlings growing in DN solution and SN solution respectively. The results show that there is no significant difference between the root lengths of the WT and the zmnlp5 mutant plants under the SN condition, which are 142.333±2.517 mm and 145.000±3.606 mm, respectively (FIG. 5). Under DN conditions, however, the root length of the zmnlp5 mutant plants is significantly shorter than that of the WT plant (166.667±8.622 mm in zmnlp5, 218.333±7.095 mm in WT, P-Values≤0.01, FIG. 5), decreased by 23.66%. Compared with the WT plant, the zmnlp5 plant accumulated 28.5% higher in the amount of nitrite in the root tip (1.106±0.077 μg/g in zmnlp5, 0.861±0.036 μg/g in WT, FIG. 5).

To sum up, in the sufficient nitrogen environment, a high $NO_3^-$ concentration conveys a signal of having sufficient external nitrogen to the plant, so that the plant roots do not need further elongation growth (the high $NO_3^-$ concentration has a certain inhibition effect on the growth of the plant root). Therefore, even though the accumulation of nitrite in the root tip of the mutant material is higher than that in the wild type material, little significant difference between the total root lengths of the mutants and the wild type plants has been observed. However, under deficient nitrogen conditions, a low $NO_3^-$ concentration conveys a signal of lack of nitrogen in the environment to the plant, so that the plant roots need a further elongation growth in order to absorb the nitrogen nutrition in the environment as much as possible. However, at this time the excessive accumulated nitrite in the root tip of the zmnlp5 mutant inhibits the normal elongation growth of the plant in the deficient nitrogen environment, resulting in the phenotype that the root length elongation of the zmnlp5 mutant in the deficient nitrogen environment is impeded. This also reduced the ability of the nitrogen assimilation in the mature plants of the zmnlp5 mutant under deficient nitrogen conditions (FIG. 3).

Therefore, the present invention cloned a gene named ZmNLP5 from maize, which plays an important regulatory role in nitrogen assimilation. The sequence of open reading frame is shown as SEQ ID NO:1. The amino acid sequence encoded by the ZmNLP5 is shown as SEQ ID NO:2. The transcription factor ZmNLP5 cloned in the present invention is mainly expressed in the root tip tissue of the maize. It improves the nitrogen assimilation of the maize by promoting the activity of the gene encoding the key enzyme (the nitrite reductase ZmNIR1.1) involved in nitrogen assimilation pathway, resulting in a increased total nitrogen content in the maize seed ultimately. The present invention is of great value in cultivating new maize varieties with high nitrogen use efficiency.

In conclusion, the maize NLP transcription factor ZmNLP5 of the present invention can promote expressions of nitrogen metabolic key enzyme genes, improve nitrogen assimilation in maize, promote elongation growth of maize root in deficient nitrogen environment, and is suitable for large-scale popularization.

Embodiment 6 A Use of the Nitrate in Promoting Expression of the ZmNLP5

Figure 6A:
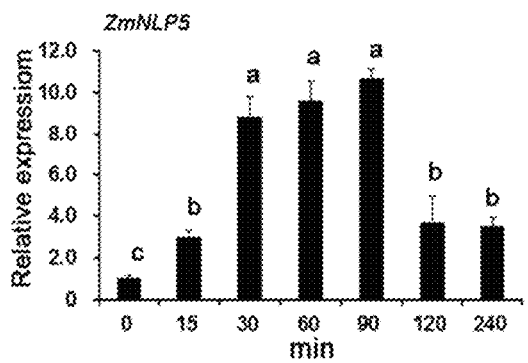
FIG. 6A shows the result of ZmNLP5 expression is stimulated by nitrate. Samples were collected from roots of N-deprived maize seedlings at 0, 15, 30, 60, 90, 120, and 240 min after supply of nitrate: mRNA levels of ZmNLP5 were measured by quantitative PCR (qPCR), with ZmUPF1 used as the internal reference gene, significant differences were indicated by letters (ANOVA; P-Values 0.05)
Figure 6B:
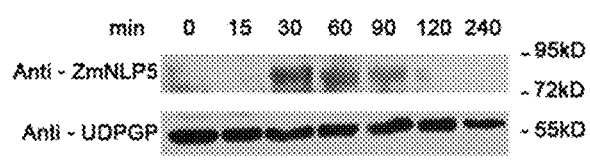
FIG. 6B shows the result of ZmNLP5 expression is stimulated by nitrate. Samples were collected from roots of N-deprived maize seedlings at 0, 15, 30, 60, 90, 120, and 240 min after supply of nitrate: Protein levels of ZmNLP5 after nitrate treatment were detected by WB, with UDPGP used as the internal reference protein.

To examine whether ZmNLP5 is responsive to nitrate, one-week-old seedlings were subjected to N starvation for two weeks and then supplied with nitrate. Samples of mRNA and protein were collected from seedling roots at a series of time points after induction of nitrate and were used for Quantitative PCR (qPCR) and immunoblot assays, respectively. The transcription level of ZmNLP5 was significantly upregulated shortly after the supply of nitrate on the nitrate-deprived plants and peaked at 90 min after treatment (FIG. 6A). The protein level of ZmNLP5 increased 30 min after nitrate supply, followed by a gradual decrease from 60 min to 90 min after induction (FIG. 6B). These results demonstrated that the expression of ZmNLP5 is rapidly and strongly stimulated by nitrate.

Embodiment 7 Overexpression of ZmNLP5 Gene Promotes Nitrogen Assimilation in Maize The ZmNLP5 cDNA isolated in Embodiment 1 was constructed into pHB vector, and was driven by the 35S promoter. The 35S::ZmNLP5 construct was transformed into a maize inbred line (B104). Taking transgenic lines in which the ZmNLP5 gene are overexpressed as examples (OE-8 and OE-11, B104 background).

Figure 7A:
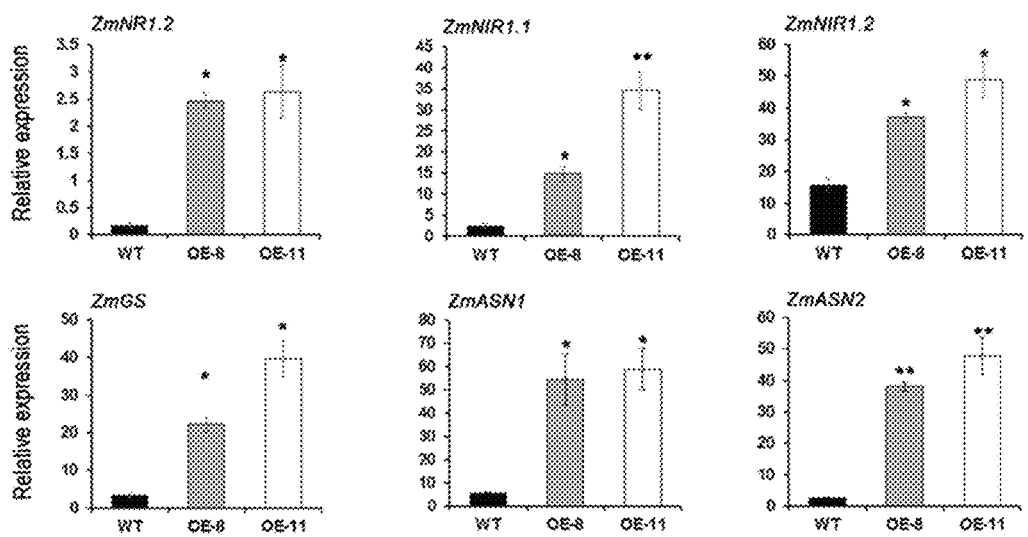
FIG. 7A shows the phenotypes of transgenic plants in which ZmNLP5 gene are overexpressed: Levels of mRNA for ZmNR1.2, ZmNIR1.1, ZmNIR1.2, ZmGS (Zea mays glutamine synthetase), ZmASN1 (Zea mays asparagine synthetase 1) and ZmASN2 (Zea mays asparagine synthetase 2) in the wild-type (WT: B104) and transgenic plants (OE-8 and OE-11) were detected by qPCR, with ZmUPF1 used as the internal reference gene, *P-Values≤0.05, ** P-Values≤0.01 by student's t-test [n=3]

In order to further clarify the effect of ZmNLP5 on the nitrogen assimilation in maize, we tested the transcriptional levels of genes encoding nitrogen metabolic key enzymes, including ZmNR, ZmNIR, ZmGS and ZJnASN, in the wild-type (WT: B104) and transgenic seedlings (OE-8 and OE-11) 30 min after nitrate stimulation. The qPCR primer pairs of the ZmNR1.2, ZmNIR1.1 and ZmNIR1.2 were described in Embodiment 4. The qPCR primer pair of the ZmGS gene is shown as SEQ ID NO:24 and SEQ ID NO:25, the qPCR primer pair of the ZmASN1 gene is shown as SEQ ID NO:26 and SEQ ID NO:27, and the qPCR primer pair of the ZmASN2 gene is shown as SEQ ID NO:28 and SEQ ID NO:29. One-week-old WT and transgenic seedlings were cultivated with DN solution for additional two weeks before treated with nitrate (15 mM $KNO_3$). The transcriptional abundance of selected genes were monitored using qPCR. For each sample, three biological replicates were performed. As shown in FIG. 7A, we detected the transcriptional levels of the six genes: ZmNR1.2, ZmNIR1.1, ZmNIR1.2, ZmGS (GRMZM5G872068), ZmASN1 (GRMZM2G074589) and ZmASN2 (GRMZM2G093175). The results show that the expression levels of the six genes in the transgenic plants are significantly higher than those in the WT plants (P-Values≤0.05), ranging from 2-17 times (FIG. 7A). The up-regulations of these nitrogen assimilation key genes in the transgenic plants indicate that the overexpression of ZmNLP5 promotes the nitrogen assimilation in maize.

Figure 7B:
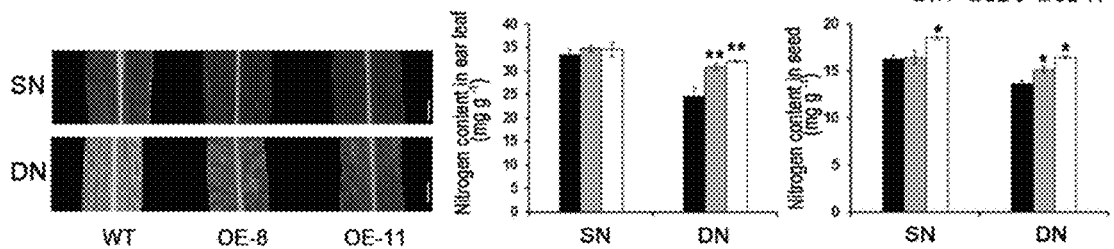
FIG. 7B shows the phenotypes of transgenic plants in which ZmNLP5 gene are overexpressed: Phenotypes of ear leaves in mature plants of WT and transgenic plants under sufficient nitrogen (SN) and deficient nitrogen (DN) conditions; the comparison diagram of the total nitrogen contents of the ear leaves and the seeds of the WT and transgenic plants under SN and DN conditions, *P-Values≤0.05, ** P-Values≤0.01 by student's t-test [n=3].

In addition, the WT and transgenic lines were planted in the soil watered with SN solution and DN solution, respectively. The total nitrogen contents of the ear leaves and the seeds were measured by the "Kjeldahl nitrogen determination method" to explore the effect of ZmNLP5 on the nitrogen assimilation in mature plants. The results showed that the total nitrogen contents in the ear leaves of the transgenic lines were significantly higher than those of the WT plant (P-Values≤0.01) under DN conditions, lifted by 25.18% (OE-8) and 30.11% (OE-11) respectively (FIG. 7B). Under SN conditions, only seed kernels of OE-11 plant accumulated more nitrogen than WT plants did (P-Values≤0.05). Under DN conditions, both transgenic lines exhibited significantly higher N contents in seed kernels compared with that in the seeds of WT (P-Values 0.05), increased by 21.81% (OE-8) and 25.65% (OE-11), respectively. These results suggested that overexpression of ZmNLP5 enhanced the ability of nitrogen assimilation in maize (FIG. 7B).

In the present specification, the present invention has been described according to the particular embodiments. But it is obvious that these embodiments can be modified or changed without departure from the spirit and scope of the present invention. Therefore, the specification and drawings described above are exemplary only and not intended to be limiting.

---

What is claimed is:

1. A method for improving nitrogen assimilation in maize, the method comprising:
   providing a ZmNLP5 cDNA having the nucleotide sequence of SEQ ID NO: 1 operably linked to a 35S promoter;
   transforming the ZmNLP5 cDNA into a maize plant; and
   measuring the nitrogen content of ear leaf and/or seed of the transformed maize plant,
   wherein the transformed maize plant exhibits increased nitrogen content of ear leaf and/or seed relative to a maize plant lacking the transformed ZmNLP5 cDNA.

2. The method of claim 1, further comprising measuring gene expression levels in the transformed maize plant, wherein the transforming the ZmNLP5 cDNA in the maize results in increased expression of a Zea mays nitrite reductase 1.1 (ZmNIR1.1) gene, a Zea mays nitrite reductase 1.2 (ZmNIR1.2) gene, a Zea mays nitrate reductase 1.2 (ZmNR1.2) gene, a Zea mays glutamine synthetase (ZmGS) gene, a Zea mays asparagine synthetase 1 (ZmASN1) gene, and a Zea mays asparagine synthetase 2 (ZmASN2) gene, as measured by gene expression levels.

3. The method of claim 1, further comprising measuring nitrogen assimilation of the transformed maize plant, wherein the transformed maize plant exhibits improved nitrogen assimilation relative to a maize plant lacking the transformed ZmNLP5 cDNA.

4. A transformed maize plant, or a part thereof, comprising a genetically transformed ZmNLP5 cDNA having the nucleotide sequence of SEQ ID NO: 1 operably linked to a 35S promoter, wherein the transformed maize plant exhibits increased nitrogen content of ear leaf and/or seed relative to a maize plant lacking the genetically transformed ZmNLP5 cDNA.

5. A seed of the transformed maize plant of claim 4, wherein the seed comprises the genetically transformed ZmNLP5 cDNA having the nucleotide sequence of SEQ ID NO: 1 operably linked to a 35S promoter.

* * * * *

SEQUENCE LISTING

```
<160> NUMBER OF SEQ ID NOS: 29

<210> SEQ ID NO 1
<211> LENGTH: 2268
<212> TYPE: DNA
<213> ORGANISM: Zea mays

<400> SEQUENCE: 1
atggacggcg tgctccagcg attcgacgtc gacctcctcc tcgacggcca cggccacggc      60
gacgacagct tatgtgggag cgagcggagg agcgcgagcg gcggcggcgc gcaggacaag     120
gcgggcatcg acggcgcggt gaaggagcgg atcgcgcggg cgctgaggat ctacaaggac     180 gcggcgggc tcgacggcgg ggcgctggtg caggtgtggg cgccggcgcg ggacggggc       240
```

-continued

```
cggcgcgtgc tggccacccg gggccagccc ttcgtgctgc cgccgccgcg gtgccaccgc     300
ctgttccagt accggacggt gtcgctcgcg cacgccttcc ccgtcggcgg cgctgccgtg     360
cccggggagc ggggcctgcc ggggcgggtg ttcgacgccg gggagcccga gtggacgccc     420
aacgtgcagt actacggcac cggcgagtac gcgcgcatca gctacgcgct catctacgac     480
atccaggccg cgctcgcgct gcccatcctt gaccccgcca cggggggcttg cctcgccgtg     540
ctcgagctcg tcaccacctc gcccaggctc cacttcgccg ccgacgtcga caggctctcc     600
gaggcgcttc aggctgtggc gttgaggggc tccgagatct gccgccgccc agcacccgag     660
gcatgcaacg acgatgggc ggcggctcag gtggccatgt cggaggttgc agacatcttg     720
aaccaagtag gcgaggctca aagctgcca ctagcgcagg cctggaccag gtgcaggcgc     780
tgcagcaccg acacggagca cgcctccctg acggctgccg cgcaccgtt ctacctcacc     840
ggcgcggacc caaacccaaa cctgctcggc ttccacgagg cctgcgtgga gcaccacctg     900
cggctacggt ccggccgggg cgggctcgtg gaggaagcgg ccgcggcgcg cggcccctc     960
ttctgcgccg acgtcaccaa gtactccatg gacgcgtacc cgctggcgca ccacgcgcgg    1020
ttctgcgaac tgtccggctg cctcgccgtg tgcgcgcggc tgcgccgcgg cggcgacgag    1080
tccatggaca cggacggcgg cggcggcgcc ggctgggacg agtgcgtgct ggagttcttc    1140
ctcccgccgg actgcaggga cggcgcgcg cagaaggcgg cagcgggcgc cgtcgcggct    1200
accatcatgg agcggtctgg cggtggcggt ctgaaggcgg tcgtgataag tgggttgcag    1260
gatttggtgt ttgacatcgc cgcagatggc gagtgcgtgc ttcggcctga tcctgtggcc    1320
atggctgatg atgttcctca gcttgagctg aacggtcatg gaggagacga gtgggactcg    1380
gatgaggag gtctgcatct ggtggtagct atgggtacca ccactacaga cattgaagca    1440
tccaagatgc accatgacga acaccatggt ggcgaggatc cgagatcaca agttggcaag    1500
aaggcggcga aaaggaaagg cgagaaaact gtcagtttgg aggaactgca gcgctacttc    1560
tctggaagcc tgaaagatgc ggccaagagt ctcggtgttt gtccgacaac gatgaagcgc    1620
atctgcaggc agcacggcat ctccaggtgg ccgttccgca agctcgccaa ggcgaaccgc    1680
tccctggaca agatcaagcg cgtcttcgag tcggtgcaag gctcatcaca ggccatggcc    1740
gccgctcctg ctcctccacc tgccgccgcc gctgcttcct attctcagca agctccagcc    1800
gtggccgctc ctccccgcgc acctgcttta tcaccatgcc tatcgagtgc tccgagagtg    1860
gcctcctccc aagcctcatg ccaagcgccg ccgccgcctc tgaaggaggc cgcatggcac    1920
aagcctttgc gcgcggggga cgccagcgtg gtcactgtca aggcgagcta cagagggggac    1980
atcgtcaggt tcagggtgcc gagctccgca ggcgtcgcga cggtgaaggg ggaggtggcc    2040
atgaggctgg ggctggcgcc cggcgagttc gacgtcaagt acctggacga tgacaacgag    2100
tgggtgctct tgtcttgcga cgccgacttc caggagtgcc tcgacgtcat cccggcgttg    2160
tcaggcgcgt cagcgtcgtc tggctccggg acggctcagc cggtggtcag gctaatggtg    2220
cacgaggtag ctgaggtcca tgggagctcc tgtggcagct cagattag                 2268
```

<210> SEQ ID NO 2
<211> LENGTH: 755
<212> TYPE: PRT
<213> ORGANISM: Zea mays

<400> SEQUENCE: 2

```
Met Asp Gly Val Leu Gln Arg Phe Asp Val Asp Leu Leu Leu Asp Gly
1               5                   10                  15
```

His Gly His Gly Asp Asp Ser Leu Cys Gly Ser Glu Arg Arg Ser Ala
            20                  25                  30

Ser Gly Gly Gly Ala Gln Asp Lys Ala Gly Ile Asp Gly Ala Val Lys
        35                  40                  45

Glu Arg Ile Ala Arg Ala Leu Arg Ile Tyr Lys Asp Ala Ala Gly Leu
 50                  55                  60

Asp Gly Gly Ala Leu Val Gln Val Trp Ala Pro Ala Arg Asp Gly Gly
 65                  70                  75                  80

Arg Arg Val Leu Ala Thr Arg Gly Gln Pro Phe Val Leu Pro Pro Pro
                85                  90                  95

Arg Cys His Arg Leu Phe Gln Tyr Arg Thr Val Ser Leu Ala His Ala
            100                 105                 110

Phe Pro Val Gly Gly Ala Ala Val Pro Gly Glu Arg Gly Leu Pro Gly
        115                 120                 125

Arg Val Phe Asp Ala Gly Glu Pro Glu Trp Thr Pro Asn Val Gln Tyr
    130                 135                 140

Tyr Gly Thr Gly Glu Tyr Ala Arg Ile Ser Tyr Ala Leu Ile Tyr Asp
145                 150                 155                 160

Ile Gln Ala Ala Leu Ala Leu Pro Ile Leu Asp Pro Ala Thr Gly Ala
                165                 170                 175

Cys Leu Ala Val Leu Glu Leu Val Thr Thr Ser Pro Arg Leu His Phe
            180                 185                 190

Ala Ala Asp Val Asp Arg Leu Ser Glu Ala Leu Gln Ala Val Ala Leu
        195                 200                 205

Arg Gly Ser Glu Ile Cys Arg Arg Pro Ala Pro Glu Ala Cys Asn Asp
    210                 215                 220

Asp Gly Ala Ala Ala Gln Val Ala Met Ser Glu Val Ala Asp Ile Leu
225                 230                 235                 240

Asn Gln Val Gly Glu Ala His Lys Leu Pro Leu Ala Gln Ala Trp Thr
                245                 250                 255

Arg Cys Arg Arg Cys Ser Thr Asp Thr Glu His Ala Ser Leu Thr Ala
            260                 265                 270

Ala Gly Ala Pro Phe Tyr Leu Thr Gly Ala Asp Pro Asn Pro Asn Leu
        275                 280                 285

Leu Gly Phe His Glu Ala Cys Val Glu His His Leu Arg Leu Arg Ser
    290                 295                 300

Gly Arg Gly Gly Leu Val Glu Glu Ala Ala Ala Ala Arg Arg Pro Leu
305                 310                 315                 320

Phe Cys Ala Asp Val Thr Lys Tyr Ser Met Asp Ala Tyr Pro Leu Ala
                325                 330                 335

His His Ala Arg Phe Cys Glu Leu Ser Gly Cys Leu Ala Val Cys Ala
            340                 345                 350

Arg Leu Arg Arg Gly Gly Asp Glu Ser Met Asp Thr Asp Gly Gly Gly
        355                 360                 365

Gly Ala Gly Trp Asp Glu Cys Val Leu Glu Phe Leu Pro Pro Asp
    370                 375                 380

Cys Arg Asp Gly Ala Ala Gln Lys Ala Ala Gly Ala Val Ala Ala
385                 390                 395                 400

Thr Ile Met Glu Arg Ser Gly Gly Gly Leu Lys Ala Val Val Ile
                405                 410                 415

Ser Gly Leu Gln Asp Leu Val Phe Asp Ile Ala Ala Asp Gly Glu Cys
        420                 425                 430

Val Leu Arg Pro Asp Pro Val Ala Met Ala Asp Asp Val Pro Gln Leu
        435                 440                 445

Glu Leu Asn Gly His Gly Gly Asp Glu Trp Asp Ser Asp Glu Glu Gly
    450                 455                 460

Leu His Leu Val Val Ala Met Gly Thr Thr Thr Thr Asp Ile Glu Ala
465                 470                 475                 480

Ser Lys Met His His Asp Glu His His Gly Gly Asp Pro Arg Ser
            485                 490                 495

Gln Val Gly Lys Lys Ala Ala Lys Arg Lys Gly Glu Lys Thr Val Ser
            500                 505                 510

Leu Glu Glu Leu Gln Arg Tyr Phe Ser Gly Ser Leu Lys Asp Ala Ala
    515                 520                 525

Lys Ser Leu Gly Val Cys Pro Thr Thr Met Lys Arg Ile Cys Arg Gln
530                 535                 540

His Gly Ile Ser Arg Trp Pro Phe Arg Lys Leu Ala Lys Ala Asn Arg
545                 550                 555                 560

Ser Leu Asp Lys Ile Lys Arg Val Phe Glu Ser Val Gln Gly Ser Ser
            565                 570                 575

Gln Ala Met Ala Ala Ala Pro Ala Pro Pro Ala Ala Ala Ala
            580                 585                 590

Ser Tyr Ser Gln Gln Ala Pro Ala Val Ala Ala Pro Arg Ala Pro
    595                 600                 605

Ala Leu Ser Pro Cys Leu Ser Ser Ala Pro Arg Val Ala Ser Ser Gln
    610                 615                 620

Ala Ser Cys Gln Ala Pro Pro Pro Leu Lys Glu Ala Ala Trp His
625                 630                 635                 640

Lys Pro Leu Arg Gly Gly Asp Ala Ser Val Val Thr Val Lys Ala Ser
            645                 650                 655

Tyr Arg Gly Asp Ile Val Arg Phe Arg Val Pro Ser Ser Ala Gly Val
            660                 665                 670

Ala Thr Val Lys Gly Glu Val Ala Met Arg Leu Gly Leu Ala Pro Gly
            675                 680                 685

Glu Phe Asp Val Lys Tyr Leu Asp Asp Asp Asn Glu Trp Val Leu Leu
690                 695                 700

Ser Cys Asp Ala Asp Phe Gln Glu Cys Leu Asp Val Ile Pro Ala Leu
705                 710                 715                 720

Ser Gly Ala Ser Ala Ser Ser Gly Ser Gly Thr Ala Gln Pro Val Val
            725                 730                 735

Arg Leu Met Val His Glu Val Ala Glu Val His Gly Ser Ser Cys Gly
            740                 745                 750

Ser Ser Asp
    755

<210> SEQ ID NO 3
<211> LENGTH: 20
<212> TYPE: DNA
<213> ORGANISM: Artificial Sequence
<220> FEATURE:
<223> OTHER INFORMATION: It is synthesized.

<400> SEQUENCE: 3
ggagtggtga gatttgggaa                                              20

<210> SEQ ID NO 4
<211> LENGTH: 23
<212> TYPE: DNA

```
<213> ORGANISM: Artificial Sequence
<220> FEATURE:
<223> OTHER INFORMATION: It is synthesized.

<400> SEQUENCE: 4
atttatgact tcagtttttg gac                                         23

<210> SEQ ID NO 5
<211> LENGTH: 22
<212> TYPE: DNA
<213> ORGANISM: Artificial Sequence
<220> FEATURE:
<223> OTHER INFORMATION: It is synthesized.

<400> SEQUENCE: 5
cacccggttg gctatgctgt ac                                          22

<210> SEQ ID NO 6
<211> LENGTH: 22
<212> TYPE: DNA
<213> ORGANISM: Artificial Sequence
<220> FEATURE:
<223> OTHER INFORMATION: It is synthesized.

<400> SEQUENCE: 6
tgtgctccac cagaaggctg ac                                          22

<210> SEQ ID NO 7
<211> LENGTH: 21
<212> TYPE: DNA
<213> ORGANISM: Artificial Sequence
<220> FEATURE:
<223> OTHER INFORMATION: It is synthesized.

<400> SEQUENCE: 7
cctggacgat gccaacgagt g                                           21

<210> SEQ ID NO 8
<211> LENGTH: 22
<212> TYPE: DNA
<213> ORGANISM: Artificial Sequence
<220> FEATURE:
<223> OTHER INFORMATION: It is synthesized.

<400> SEQUENCE: 8
tcccatggac ctcagctacc tc                                          22

<210> SEQ ID NO 9
<211> LENGTH: 46
<212> TYPE: DNA
<213> ORGANISM: Artificial Sequence
<220> FEATURE:
<223> OTHER INFORMATION: It is synthesized.

<400> SEQUENCE: 9
caggtcgact ctagaggatc catggacggc gtgctccagc gattcg                46

<210> SEQ ID NO 10
<211> LENGTH: 43
<212> TYPE: DNA
<213> ORGANISM: Artificial Sequence
<220> FEATURE:
<223> OTHER INFORMATION: It is synthesized.

<400> SEQUENCE: 10
gggaaattcg agctcggtac catctgagct gccacaggag ctc                   43
```

<210> SEQ ID NO 11
<211> LENGTH: 28
<212> TYPE: DNA
<213> ORGANISM: Artificial Sequence
<220> FEATURE:
<223> OTHER INFORMATION: It is synthesized.

<400> SEQUENCE: 11
cccaagcttg caagcacgca gattcgca                                      28

<210> SEQ ID NO 12
<211> LENGTH: 27
<212> TYPE: DNA
<213> ORGANISM: Artificial Sequence
<220> FEATURE:
<223> OTHER INFORMATION: It is synthesized.

<400> SEQUENCE: 12
cgggatccag cggtagcggt ggcagtg                                       27

<210> SEQ ID NO 13
<211> LENGTH: 1267
<212> TYPE: DNA
<213> ORGANISM: Zea mays

<400> SEQUENCE: 13
gcaagcacgc agattcgcag acacgatgga tctcccgacc ccgtctgtcg ccgtccctgg     60
gatgctcaga cctgttatcc cggccgccgg caaggatgcg acgtgaagcc actccagtcc    120
tctccctact cccgctgctc ccctcctatc gtcgctctgg agacagatct gctcgccgtc    180
cccggtcctc cttgttgcca tcccttacct cctccagggc tcgtggccga dacgcgcccc    240
cgggcgggga aggttggcgt tgtccaagag gcggccgcgc gccccgctgt ctggcacatg    300
acgatggatg tgcacggccg cacaggacac gtcgcccgcc cttgcacgcg catcaaagga    360
caaaggccgg tcgcggcgta tggcctgggc tccaaacgtg tggccgctgg agcccccaa     420 gccaaggcac ggtgccatct cggccgttgc tgcctgctcg gtaagccctg gctcaatgtc    480
atgcaagtaa gcagcccagt agtaccgggc gacccggttc gaccagatgg acgcagcagg    540
agctatcaga gagaagccag tgcacggcac gcctcgcgcc ggacccggtc ccgtgcgcgg    600
gcgtctcgcc gacgagcgac accgacaccg acccctttggg cggctcatgg ggcgccttgc   660
attgccggtg tatctatcac gggttcatgt acgtggcctc ggtgtcccca catgcttgcc    720
gcctgcgcct ggccaaactt tccggctctt cttggctctg cttcagcaat aagcaagcag    780
cggccgaaac tggggcagct cttttccgcc cctgtctccc ccctggtaac ggttttggtg    840
gtctccgggt ccacttggat agatgtgaac gtgtcagtat gtactctcca gaaaatcgag    900
cttccattgc tttagagagg cagatgcata tataattctt gaaacgccgc gctgtttctc    960
aacgtaggta gcctctgtca acgcgataca gcagtaaaca tgagtacaac gtgagctcag   1020
agccgtccat ggcgtacgag ggcacgtcgg taaaatctca acgtcccgtc ccgtgcctgc   1080
ctgccatttc gattagttag aggagctgcg cctgcgtctg cctgcccccct tgaactcccc  1140 aagagccaag aaccagcgca gcagcgcgcc ccctcccccgc cccacaataa aacagccaca   1200
cgctcgccac ccatggccac caccaccacc accaccacag cacaggccca ctgccaccgc   1260
taccgct                                                            1267

<210> SEQ ID NO 14

```
<211> LENGTH: 28
<212> TYPE: DNA
<213> ORGANISM: Artificial Sequence
<220> FEATURE:
<223> OTHER INFORMATION: It is synthesized.

<400> SEQUENCE: 14
cccaagcttg caagcacgca gattcgca                                              28

<210> SEQ ID NO 15
<211> LENGTH: 27
<212> TYPE: DNA
<213> ORGANISM: Artificial Sequence
<220> FEATURE:
<223> OTHER INFORMATION: It is synthesized.

<400> SEQUENCE: 15
cgggatccag cggtagcggt ggcagtg                                               27

<210> SEQ ID NO 16
<211> LENGTH: 20
<212> TYPE: DNA
<213> ORGANISM: Artificial Sequence
<220> FEATURE:
<223> OTHER INFORMATION: It is synthesized.

<400> SEQUENCE: 16
gatcaaagga tacgcatact                                                      20

<210> SEQ ID NO 17
<211> LENGTH: 20
<212> TYPE: DNA
<213> ORGANISM: Artificial Sequence
<220> FEATURE:
<223> OTHER INFORMATION: It is synthesized.

<400> SEQUENCE: 17
tcgacgtcga cggaccagaa                                                      20

<210> SEQ ID NO 18
<211> LENGTH: 20
<212> TYPE: DNA
<213> ORGANISM: Artificial Sequence
<220> FEATURE:
<223> OTHER INFORMATION: It is synthesized.

<400> SEQUENCE: 18
ccaaccaagt acggcaagta                                                      20

<210> SEQ ID NO 19
<211> LENGTH: 21
<212> TYPE: DNA
<213> ORGANISM: Artificial Sequence
<220> FEATURE:
<223> OTHER INFORMATION: It is synthesized.

<400> SEQUENCE: 19
gcccatgagg ttacagatga g                                                    21

<210> SEQ ID NO 20
<211> LENGTH: 20
<212> TYPE: DNA
<213> ORGANISM: Artificial Sequence
<220> FEATURE:
<223> OTHER INFORMATION: It is synthesized.

<400> SEQUENCE: 20
```
ctggaccgga tgccccaaca                                               20

<210> SEQ ID NO 21
<211> LENGTH: 20
<212> TYPE: DNA
<213> ORGANISM: Artificial Sequence
<220> FEATURE:
<223> OTHER INFORMATION: It is synthesized.

<400> SEQUENCE: 21
cgacgcggcc gcccacgaag                                               20

<210> SEQ ID NO 22
<211> LENGTH: 20
<212> TYPE: DNA
<213> ORGANISM: Artificial Sequence
<220> FEATURE:
<223> OTHER INFORMATION: It is synthesized.

<400> SEQUENCE: 22
cgacacgcgc ccctacacca                                               20

<210> SEQ ID NO 23
<211> LENGTH: 20
<212> TYPE: DNA
<213> ORGANISM: Artificial Sequence
<220> FEATURE:
<223> OTHER INFORMATION: It is synthesized.

<400> SEQUENCE: 23
gatcacgcac acgttccatt                                               20

<210> SEQ ID NO 24
<211> LENGTH: 19
<212> TYPE: DNA
<213> ORGANISM: Artificial Sequence
<220> FEATURE:
<223> OTHER INFORMATION: It is synthesized.

<400> SEQUENCE: 24
tcctgctcaa taccatacc                                                19

<210> SEQ ID NO 25
<211> LENGTH: 18
<212> TYPE: DNA
<213> ORGANISM: Artificial Sequence
<220> FEATURE:
<223> OTHER INFORMATION: It is synthesized.

<400> SEQUENCE: 25
gtgatgtgcg attgctac                                                 18

<210> SEQ ID NO 26
<211> LENGTH: 22
<212> TYPE: DNA
<213> ORGANISM: Artificial Sequence
<220> FEATURE:
<223> OTHER INFORMATION: It is synthesized.

<400> SEQUENCE: 26
aagctgttga atgggacgca tc                                            22

<210> SEQ ID NO 27
<211> LENGTH: 20
<212> TYPE: DNA

```
<213> ORGANISM: Artificial Sequence
<220> FEATURE:
<223> OTHER INFORMATION: It is synthesized.

<400> SEQUENCE: 27
tggctgaagc aacgggtgtc                                                  20

<210> SEQ ID NO 28
<211> LENGTH: 21
<212> TYPE: DNA
<213> ORGANISM: Artificial Sequence
<220> FEATURE:
<223> OTHER INFORMATION: It is synthesized.

<400> SEQUENCE: 28
ccgcctacga acaccaacat g                                                21

<210> SEQ ID NO 29
<211> LENGTH: 21
<212> TYPE: DNA
<213> ORGANISM: Artificial Sequence
<220> FEATURE:
<223> OTHER INFORMATION: It is synthesized.

<400> SEQUENCE: 29
acagccggtg gacacagata c                                                21
```